US009845499B2

(12) United States Patent
Hung et al.

(10) Patent No.: US 9,845,499 B2
(45) Date of Patent: Dec. 19, 2017

(54) MICROFLUIDIC SIPHONING ARRAY FOR NUCLEIC ACID QUANTIFICATION

(71) Applicant: Combinati Incorporated, Palo Alto, CA (US)

(72) Inventors: Ju-Sung Hung, Palo Alto, CA (US); Andrew Zayac, San Leandro, CA (US); Megan Dueck, San Diego, CA (US)

(73) Assignee: COMBINATI INCORPORATED, Palo Alto, CA (US)

( * ) Notice: Subject to any disclaimer, the term of this patent is extended or adjusted under 35 U.S.C. 154(b) by 0 days.

(21) Appl. No.: 15/363,896

(22) Filed: Nov. 29, 2016

(65) Prior Publication Data

US 2017/0283855 A1     Oct. 5, 2017

Related U.S. Application Data

(60) Provisional application No. 62/317,993, filed on Apr. 4, 2016.

(51) Int. Cl.
*B01L 3/00*     (2006.01)
*C12Q 1/68*     (2006.01)

(52) U.S. Cl.
CPC .......... *C12Q 1/686* (2013.01); *B01L 3/50273* (2013.01); *B01L 3/502707* (2013.01); *B01L 3/502715* (2013.01); *B01L 2200/12* (2013.01); *B01L 2300/041* (2013.01); *B01L 2300/0832* (2013.01); *B01L 2300/0864* (2013.01); *B01L 2300/12* (2013.01); *B01L 2400/0487* (2013.01)

(58) Field of Classification Search
None
See application file for complete search history.

(56) References Cited

U.S. PATENT DOCUMENTS 5,807,522 A     9/1998  Brown et al.
8,871,446 B2   10/2014  Hong et al.
(Continued)

FOREIGN PATENT DOCUMENTS

WO   WO-2015085171 A1   6/2015
WO   WO-2015085181 A1   6/2015

OTHER PUBLICATIONS

Beer NR. et al, "On-Chip, Real-Time, Single-Copy Polymerase Chain Reaction in Picoliter Droplets," Anal. Chem. 2007, 79, 8471-8475.
(Continued)

*Primary Examiner* — Robert Xu
(74) *Attorney, Agent, or Firm* — Wilson Sonsini Goodrich & Rosati

(57) ABSTRACT

A microfluidic device can have a plurality of microchambers connected to a microchannel via siphon apertures. The microfluidic device may be formed from a thermoplastic and capped by a thermoplastic thin film. The microfluidic device may be used for digital polymerase chain reactions by forcing reagent into the microchambers at low pressure via an inlet, forcing any gas trapped in the microfluidic device to outgas through the thin film by applying high pressure to the microfluidic device via inlets and outlets of the microfluidic device, and applying air at low pressure to the inlets in order to digitize the chambers such that the reagent in each chamber is isolated from the reagent in other chambers by an air gap. After digitization, the device may be used to run a digital polymerase chain reaction process.

18 Claims, 8 Drawing Sheets

(56) References Cited

U.S. PATENT DOCUMENTS 9,213,042 B2    12/2015   Oldham et al.
2009/0250347 A1   10/2009   Powell et al.
2014/0291558 A1   10/2014   Laermer et al.

OTHER PUBLICATIONS

Men Y. et al, "Digital Polymerase Chain Reaction in an Array of Femtoliter Polydimethylsiloxane Microreactors," Anal. Chem. 2012, 84, 4262-4266, 10 pages.
Morrison T. et al, "Nanoliter High Throughput Quantitative PCR," Nucleic Acids Research, 2006, 34, 18, e123, 9 pages.
Ottesen, et al. "Microfluidic Digital PCR Enables Multigene Analysis of Individual Environmental Bacteria," Science, Dec. 1, 2006, 314,1464-1467.
Saiki RK. et al, "Primer-Directed Enzymatic Amplification of DNA with a Thermostable DNA Polymerase," Science, Jan. 29, 1988, 239,487-491.
Shen F. et al, "Digital PCR on a SlipChip," Lab Chip, 2010, 10, 2666-2672, 9 pages.
Volgelstein, B. et al, "Digital PCR," Proc. Natl. Acad. Sci USA, Aug. 1999, 96, 9236-9241.
Espira, Inc., "Digital PCR," <http://www.espirainc.com/digital-pcr.html>, [dated Feb. 15, 2017], 1 page.
Formulatrix, "Constellation Digital PCR," <http://formulatrix.com/pcr/index.html>, [dated Feb. 15, 2017], 3 pages.
Stilla, "Crystal Digital PCR," http://www.stilla.fr/index.html#crystal-digital-pcr <http://www.stilla.fr/index.html>,[dated Feb. 15, 2017], 6 pages.
JN Medsys, "Clarity™ Digital PCR Technology," <http://www.jnmedsys.com/digital-pcr-description/>, [dated Feb. 15, 2017], 11 pages.
Ramakrishnan et al. Integrated Fluidic Circuits (IFCs) for digital PCR. Methods Mol Biol 949:423-431 (2013).

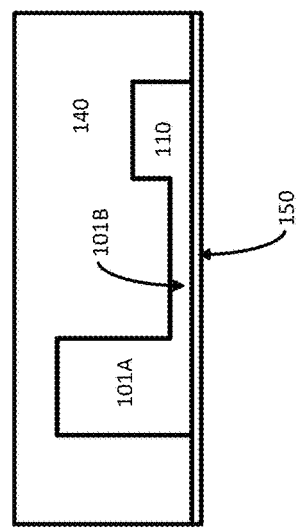
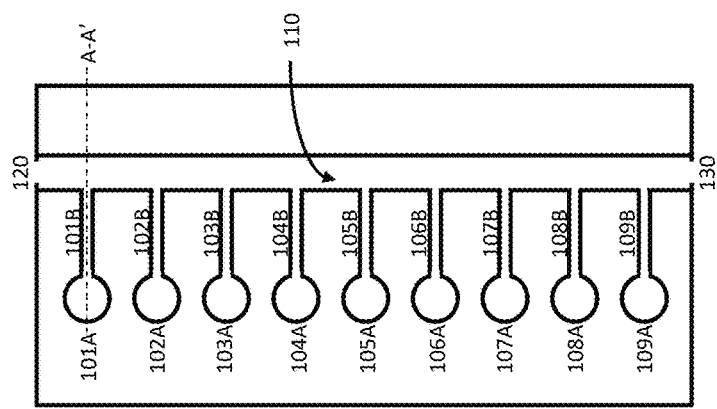
FIG. 1B
FIG. 1A

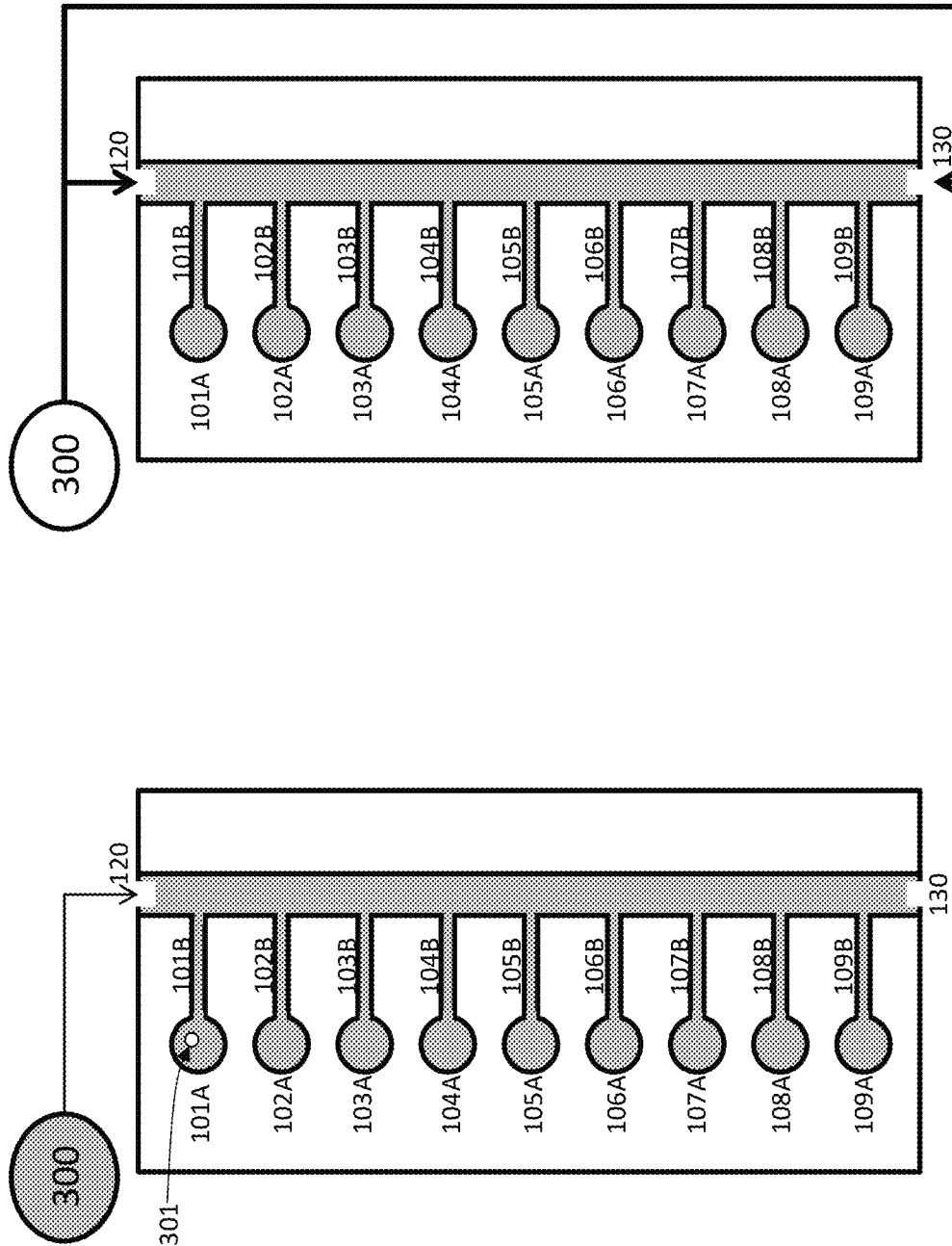

MICROFLUIDIC SIPHONING ARRAY FOR NUCLEIC ACID QUANTIFICATION

CROSS REFERENCE TO RELATED APPLICATIONS

This application claims benefit of priority to U.S. Provisional Application Ser. No. 62/317,993 titled "Microfluidic Siphoning Array for Nucleic Acid Quantification" filed on Apr. 4, 2016, which is incorporated by reference in its entirety herein.

STATEMENT OF GOVERNMENT INTEREST

This invention was made with government support under Small Business Innovation Research grant number 1R43OD023028-01 awarded by the National Institute of Health. The government has certain rights in the invention.

FIELD

The present disclosure relates generally to microfluidic structures such as thermoplastic microfluidic structures. Such structures may be used in nucleic acid quantification by digital polymerase chain reaction (dPCR).

BACKGROUND

Microfluidic devices are devices that contain structures that handle fluids on a small scale. Typically, a microfluidic device operates on a sub-millimeter scale and handles micro-liters, nano-liters, or smaller quantities of fluids. In microfluidic devices, a major fouling mechanism is trapped air, or bubbles, inside the micro-structure. This can be particularly problematic when using a thermoplastic material to create the microfluidic structure, as the gas permeability of thermoplastics is very low.

In order to avoid fouling by trapped air, previous microfluidic structures use either simple straight channel or branched channel designs with thermoplastic materials, or else manufacture the device using high gas permeability materials such as elastomers. However, simple designs limit possible functionality of the microfluidic device, and elastomeric materials are both difficult and expensive to manufacture, particularly at scale.

One application of microfluidic structures is in dPCR. dPCR dilutes a nucleic acid sample down to one or less nucleic acid template in each partition of a microfluidic structure providing an array of many partitions, and performs a PCR reaction across the array. By counting the partitions in which the template was successfully PCR amplified and applying Poisson statistics to the result, the target nucleic acid is quantified. Unlike the popular quantitative real-time PCR (qPCR) where templates are quantified by comparing the rate of PCR amplification of an unknown sample to the rate for a set of known qPCR standards, dPCR has proven to exhibit higher sensitivity, better precision and greater reproducibility.

For genomic researchers and clinicians, dPCR is particularly powerful in rare mutation detection, quantifying copy number variants, and Next Gen Sequencing library quantification. The potential use in clinical settings for liquid biopsy with cell free DNA and viral load quantification further increases the value of dPCR technology. Existing dPCR solutions have used elastomeric valve arrays, silicon through-hole approaches, and microfluidic encapsulation of droplets in oil. Despite the growing number of available dPCR platforms, dPCR has been at a disadvantage when compared to the older qPCR technology which relies on counting the number of PCR amplification cycles. The combination of throughput, ease of use, performance and cost are the major barriers for gaining adoption in the market for dPCR.

SUMMARY

Embodiments of the present disclosure include a device comprising a microchannel comprising at least one inlet and at least one outlet, a plurality of microchambers and siphon apertures, wherein each microchamber connects to the microchannel via a siphon aperture, and a thermoplastic thin film applied to a surface of the microfluidic device such that the thin film caps the microchannel, microchambers, and siphon apertures. In some embodiments, the microchannel comprises a plurality of sub-channels connected via a cross-channel and the microchambers connect to the sub-channels. In further embodiments, the plurality of sub-channels are parallel to one another such that the microchambers form a grid of microchambers. In some embodiments, the device further comprises a pneumatic pump connected to the at least one inlet and the at least one outlet.

In some embodiments of the device, the siphon apertures are of approximately 5 micrometers in height. In some embodiments, the thin film is approximately 100 micrometers in thickness. In some embodiments, the thermoplastic comprises a cyclo-olefin polymer and the thin film comprises a cyclo-olefin polymer thin film.

In some embodiments of the device, the microchambers are filled with a reagent for polymerase chain reaction. In some embodiments, the number of microchambers is between 1,000 and 20,000. In one embodiment, the number of microchambers is 2000. In some embodiments, the microchambers are hemispherical in shape. In other embodiments, the microchambers are cylindrical in shape.

Embodiments of the present disclosure also include a method for forming a microfluidic device comprising injection molding thermoplastic to create a microfluidic structure comprising a plurality of microchambers connected to one another via at least one microchannel, wherein each microchamber further comprises a siphon aperture connecting the microchamber to the at least one microchannel and capping the microfluidic structure with a thin film.

In some embodiments of the method, the thin film is applied to the microfluidic structure created by injection molding. In other embodiments, the thin film is formed as part of the injection molding process. In some embodiments of the method, the microfluidic structure further comprises at least one inlet connected to the at least one microchannel and at least one outlet connected to the at least one microchannel.

In some embodiments, the method further comprises applying low pressure to the at least one inlet to fill the plurality of microchambers with reagent, applying high pressure to the at least one inlet and the at least one outlet to force gas within the plurality of microchambers to pass through the thin film, and applying a low pressure at the at least one inlet to introduce a gas into the microchannel without introducing a gas into the plurality of microchambers.

Embodiments of the present disclosure also include a method for using a microfluidic device comprising filling a plurality of microchambers of a microfluidic device with reagent by applying low pressure to at least one inlet connected to a microchannel, wherein the microchannel is connected to the plurality of microchambers by a plurality of siphon apertures, applying a high pressure at the at least one inlet and at at least one outlet to force gas within the plurality of microchambers to pass through a thin film capping the plurality of microchambers, the plurality of siphon apertures, and the microchannel, and applying a low pressure at the at least one inlet to introduce a gas into the microchannel without introducing a gas into the plurality of microchambers.

Embodiments of the method for using a microfluidic device may further comprise performing a polymerase chain reaction within each of the plurality of microchambers, counting the number of microchambers within which the polymerase chain reaction successfully amplified the reagent, and applying Poisson statistics to the counted number of microchambers to quantify nucleic acids within the reagent. In some embodiments, this method is performed using a single integrated machine.

Other features and advantages will become apparent from the following detailed description and drawings.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure, but are intended to be illustrative only.

FIGS. 1A and 1B show an example of a microfluidic structure according to embodiments of the present disclosure. FIG. 1A shows the structure from an overhead view, while FIG. 1B illustrates a cross-section of the structure.

FIG. 2A illustrates an embodiment in which parallel sub-channels and one or more cross-channels are used to form a grid of microchambers. FIG. 2B illustrates an embodiment in which a single microchannel in a serpentine pattern forms a hexagonal grid of microchambers.

FIGS. 3A-3D illustrate a method for use of the microfluidic device shown in FIGS. 1A and 1B. FIG. 3A illustrates a step of applying reagent at low pressure, FIG. 3B illustrates a step of applying a high pressure across the microfluidic device to force outgassing, FIG. 3C illustrates a step of applying air at low pressure, and FIG. 3D illustrates the state of the system after the completion of the method.

DESCRIPTION

Figure 2A:
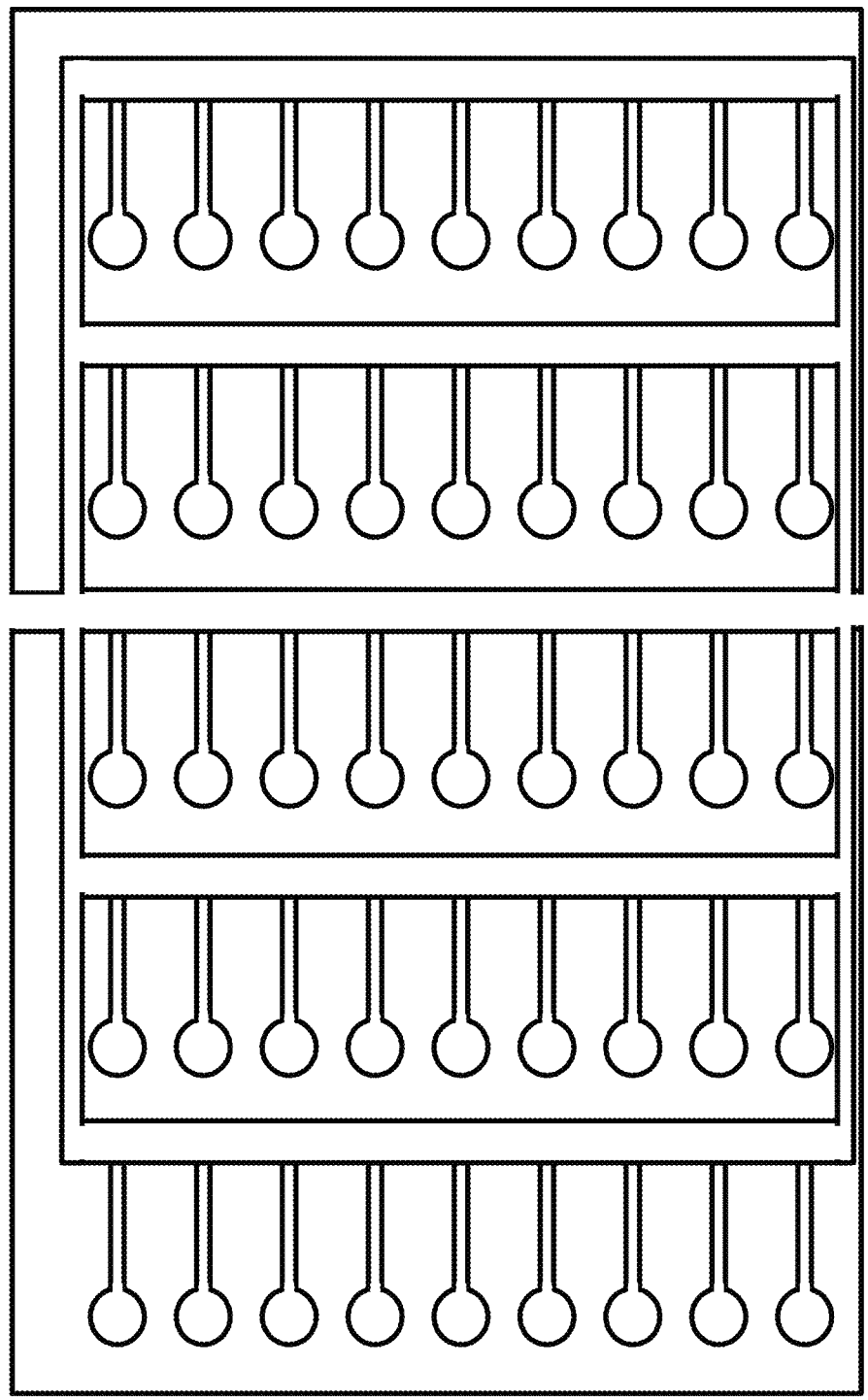
FIGS. 2A and 2B illustrate potential arrangements of microchambers, siphon apertures, and microchannels within a microfluidic device according to embodiments of the present disclosure.

The present disclosure describes a microfluidic structure that provides microfluidic structures formed out of a thermoplastic, incorporating a thin film to allow for pressurized outgassing while serving as a gas barrier when pressure is released. The use of thermoplastic to form the microfluidic structure allows the use of the inexpensive and highly scalable injection molding process, while the thin film provides the ability to outgas via pressurization, avoiding the fouling problems in some microfluidic structures that do not incorporate thin films. One use for this structure is a microfluidic design incorporating an array of dead-ended microchambers connected by microchannels, formed out of thermoplastics. This design can be used in a digital PCR application to partition reagents into the array of microchambers and thereby used to quantify nucleic acids in digital PCR.

FIGS. 1A and 1B show an example of a microfluidic structure 100 according to embodiments of the present disclosure.

FIG. 1A shows the structure from an overhead view, while FIG. 1B illustrates a cross-section of the structure along the line marked A-A'. In FIG. 1A, the illustrated structure includes microchambers 101A, 102A, . . . and siphon apertures 101B, 102B, . . . . In addition, the microchambers connect to a microchannel 110 via the siphon apertures. Microchannel 110 has an inlet 120 and an outlet 130. A number of microchambers may be formed in the microfluidic device. In some embodiments, the number of microchambers is between 10,000 and 30,000. In one embodiment, the number is 20,000. In some embodiments, multiple inlets and outlets may be provided.

In FIG. 1B, the structure of a single microchamber 101A is shown, as connected to the microchannel 110 by siphon aperture 101B. FIG. 1B also illustrates the thermoplastic 140 used to form the microfluidic structure, and the thin film 150 used to cap the microfluidic structure. The thin film is gas impermeable at low pressures, but allows for outgassing through the thin film when pressure is applied. In an exemplary embodiment of the present disclosure, both the thermoplastic 140 and the thin film 150 are composed of a cyclo-olefin polymer. One suitable thermoplastic is Zeonor 1430R from Zeon Chemical, while one suitable thin film is Zeonox 1060R from Zeon Chemical. In other embodiments, the thin film is a material that is gas-impermeable at low pressure and at least partially gas permeable under pressure. In at least some embodiments of the present disclosure, the thin film is approximately 100 micrometers in thickness. In some embodiments, the siphon aperture is 5 micrometers high. In some embodiments, the microchamber is 60 micrometers in diameter and 40 micrometers in height. In some embodiments, the microchamber is 30 micrometers in diameter and 100 micrometers in height. In some embodiments, the microchamber is cylindrical in shape.

Figure 2B:
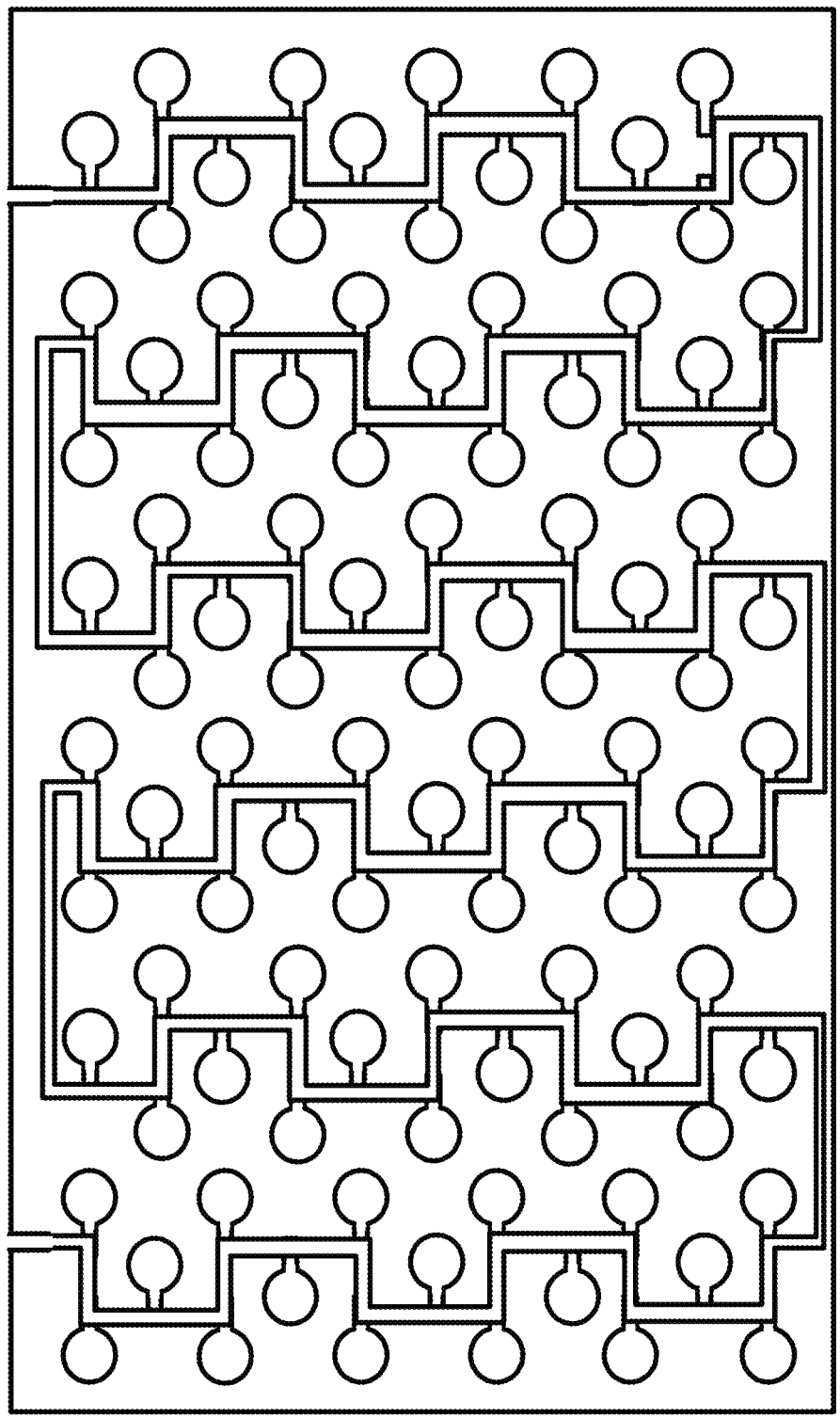

FIGS. 2A and 2B illustrate potential arrangements of microchambers, siphon apertures, and microchannels within a microfluidic device according to embodiments of the present disclosure. In some embodiments, multiple microchannels are employed, while in other embodiments, a single microchannel may be used, including a microchannel formed of a group of sub-channels and one or more cross-channels connecting the subchannels. In some of these embodiments, the sub-channels are parallel to one another so that the array of microchambers forms a grid of microchambers. FIG. 2A illustrates an embodiment in which parallel sub-channels and one or more cross-channels are used to form a grid of microchambers.

In other embodiments, microchambers are constructed so as to form a hexagonal grid of microchambers, with curved or angled sub-channels connecting the microchambers. A hexagonal grid of microchambers may also be formed and connected by a single microchannel, such as by a microchannel that forms a serpentine pattern across the microfluidic device. FIG. 2B illustrates an embodiment in which a single microchannel in a serpentine pattern forms a hexagonal grid of microchambers.

Figure 3D:
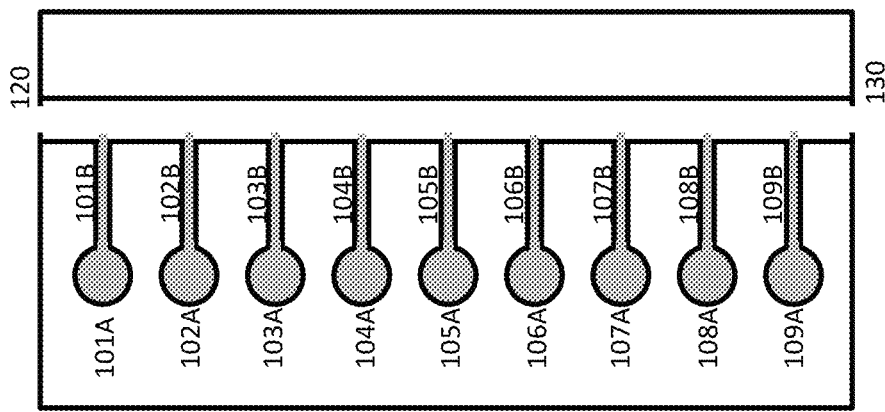

FIGS. 3A-3D illustrate a method for use of the microfluidic device shown in FIGS. 1A and 1B. In FIG. 3A, a low pressure is applied to reagent at the inlet 120 via a pneumatic pump 300 to force reagent into the microchannel 110 and thereby fill the microchambers via the siphon apertures. In some embodiments, low pressure may be from 1 to 4 psi. The pressure forces reagent to flow through the microchannel, and thereby to flow into the microchambers via the siphon apertures. At this time, gas bubbles such as bubble 301 may remain within the microchambers, siphon apertures, or microchannel. This filling via the application of low pressure may continue until the microchambers, siphon apertures, and microchannel are substantially filled with reagent. The reagent may be a reagent to be used in a polymerase chain reaction. In some embodiments, the reagent is diluted such that no more than one PCR template is present in the reagent per microchamber of the microfluidic device.

In FIG. 3B, the pneumatic pump is connected to both inlets and outlets and a high pressure is applied. In some embodiments, high pressure may be from 8 psi up to 16 psi. The high pressure is transmitted via the reagent and applied to gas bubbles such as bubble 301. Under the influence of this high pressure, thin film 150 becomes gas permeable, and the bubble 301 can outgas through the thin film 150. By applying this high pressure, the microchambers, siphon apertures, and microchannels can be rendered substantially free of gas bubbles, thereby avoiding fouling.

Figure 3C:
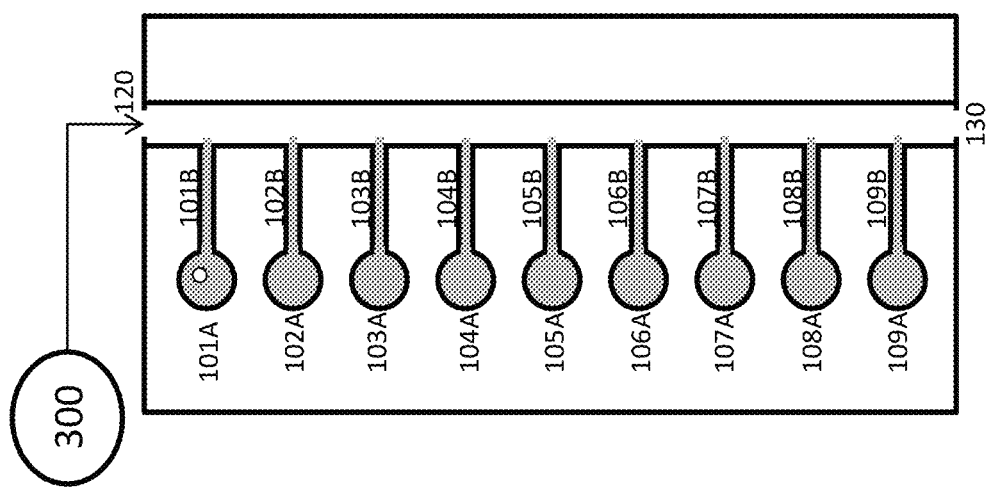

In FIG. 3C, air is reintroduced by applying low pressure to a gas at the inlet 120 via pneumatic pump 300. This air pressure is not sufficient to allow the gas to outgas through the thin film, and is also not high enough to force gas bubbles into the siphon apertures and microchambers. Instead, the gas clears the microchannel of reagent, leaving the reagent isolated in each microchamber and siphon aperture. In some embodiments, the gas is air. In other embodiments, the gas may be a gas such as nitrogen, carbon dioxide, or a noble gas. Such a gas may be used to avoid reaction between the reagent and the component gases of air.

FIG. 3D illustrates the state of the system after the low pressure has been applied in FIG. 3C. As can be seen, the microchambers and siphon apertures remain filled with reagent, while the microchannel is clear. The siphon apertures create a high surface tension of the reagent, preventing it from flowing into the microchannel and minimizing evaporation of reagent.

Figure 4:
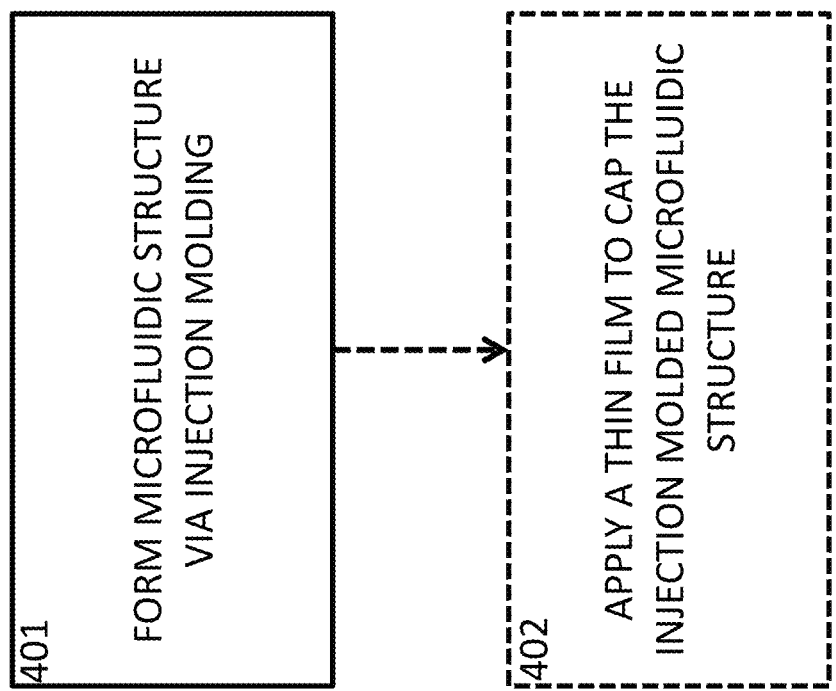
FIG. 4 illustrates a method of manufacture of embodiments of the present disclosure.

FIG. 4 illustrates a method of manufacture of embodiments of the present disclosure. In FIG. 4, an injection molding process 401 is used to form a microfluidic structure. The microfluidic structure includes an array of microchambers, which are connected to at least one microchannel via siphon apertures, as shown in FIGS. 1A and 1B. The microfluidic structure is capped by a thin film. In the capping process, openings in at least one side of the microstructure are covered over in order to close the microstructures. In some embodiments of the present disclosure, the capping is performed by a process 402 of applying a thin film to the injection molded microfluidic structure. In other embodiments of the present disclosure, the capping is performed by forming the thin film as part of the injection molding process 401.

Figure 5:
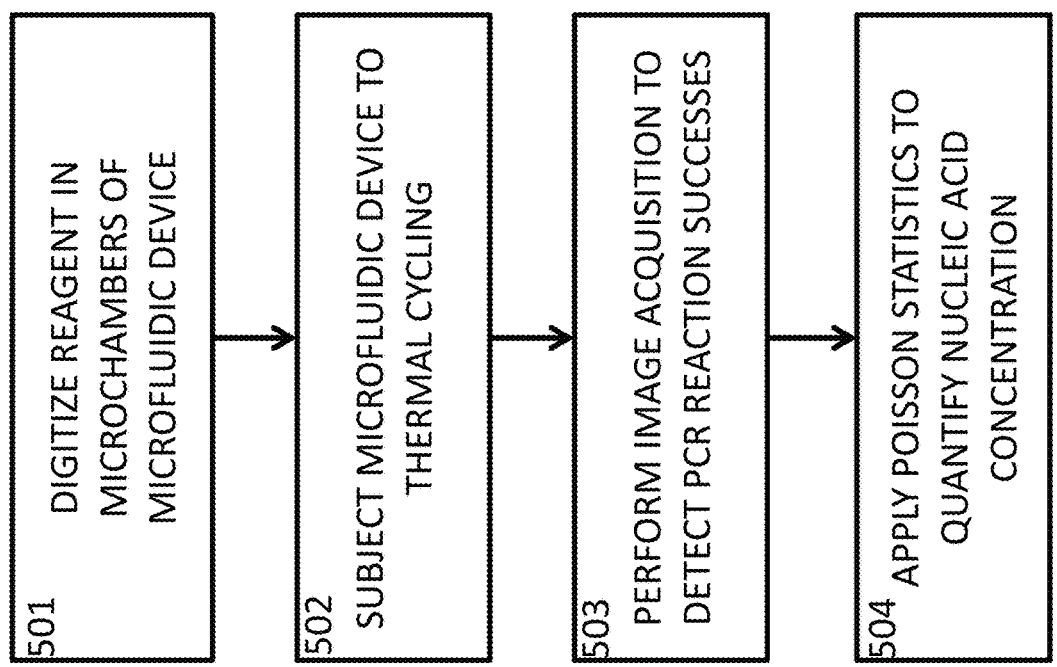
FIG. 5 illustrates a digital PCR process to be employed with the above-described microfluidic device.

FIG. 5 illustrates a digital PCR process to be employed with the above-described microfluidic device. In step 501, reagent is digitized as shown in FIGS. 3A-3D. In step 502, the reagent is subjected to thermal cycling to run the PCR reaction on the reagent in the microchambers. This step may be performed, for example, using a flat block thermal cycler. In step 503, image acquisition is performed to determine which microchambers have successfully run the PCR reaction. Image acquisition may, for example, be performed using a three color probe detection unit. In step 504, Poisson statistics are applied to the count of microchambers determined in step 503 to convert the raw number of positive chambers into a nucleic acid concentration.

Figure 6:
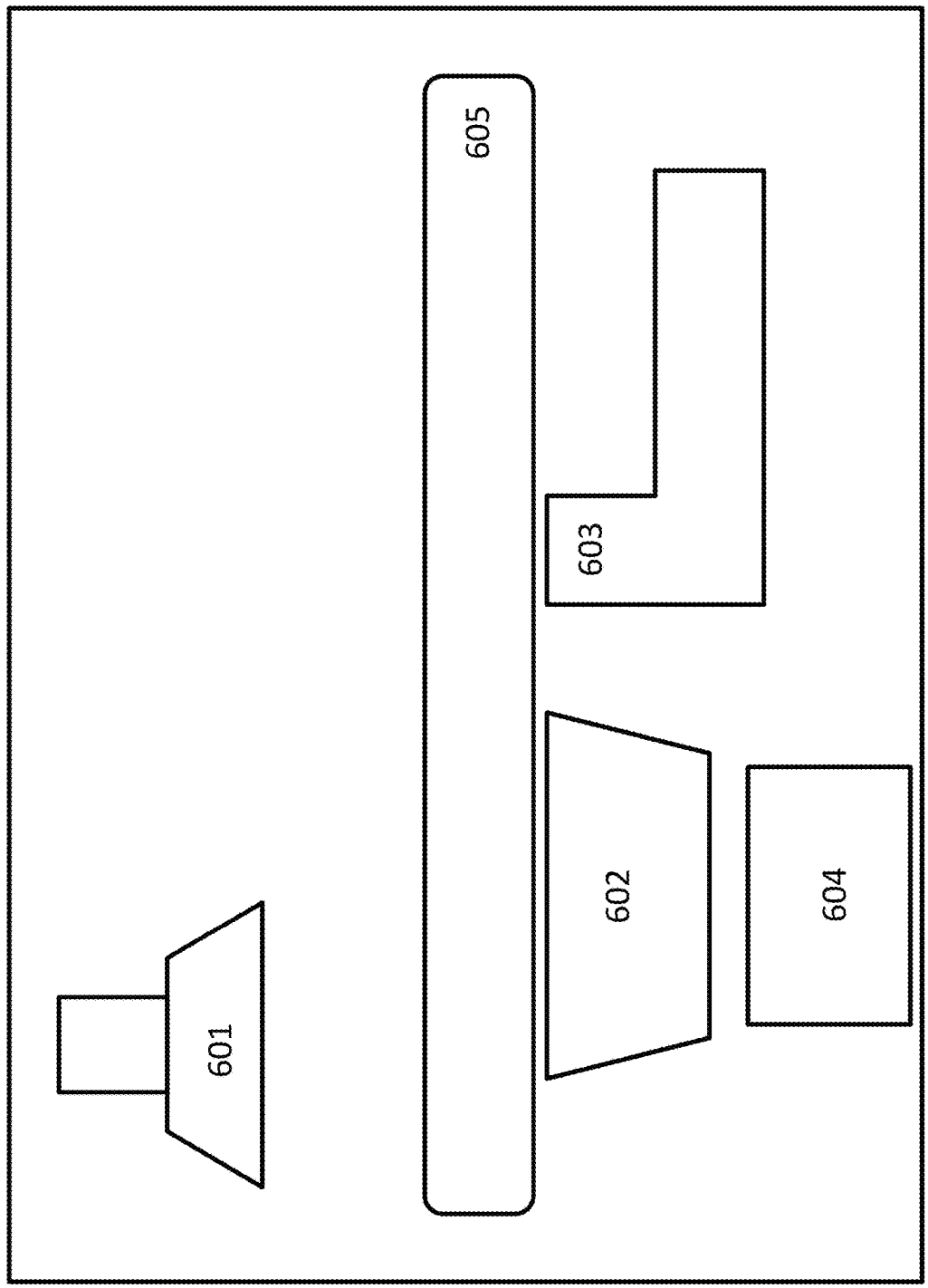
FIG. 6 illustrates a machine 600 for performing the process of FIG. 5 in a single machine.

FIG. 6 illustrates a machine 600 for performing the process of FIG. 5 in a single machine. The machine 600 includes a pneumatic module 601, which contains pumps and manifolds and may be moved in a Z-direction, operable to perform the application of pressure as described in FIGS. 3A-3D. Machine 600 also includes a thermal cycler 602, such as a flat block thermal cycler, to thermally cycle the microfluidic device and thereby cause the polymerase chain reaction to run. Machine 600 further includes an optical module 603, such as an epi-fluorescent optical module, which can optically determine which microchambers in the microfluidic device have successfully run the PCR reaction. The optical module 603 may feed this information to a processor 604, which uses Poisson statistics to convert the raw count of successful microchambers into a nucleic acid concentration. A transfer stage 605 may be used to move a given microfluidic device between the various modules and to handle multiple microfluidic devices simultaneously. The microfluidic device described above, combined with the incorporation of this functionality into a single machine, reduces the cost, workflow complexity, and space requirements for dPCR over other implementations of dPCR.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings.

For example, while described in the context of a dPCR application, a person of ordinary skill in the art would understand that other microfluidic devices which require a number of isolated microchambers filled with a liquid that are isolated via a gas may benefit from the use of a thin thermoplastic film to allow outgassing to avoid gas fouling while also providing an advantage with respect to manufacturability and cost. Other than PCR, other nucleic acid amplification methods such as loop mediated isothermal amplification can be adapted to perform digital detection of specific nucleic acid sequences according to embodiments of the present disclosure. The microchambers can also be used to isolate single cells with the siphoning apertures designed to be close to the diameter of the cells to be isolated. In another embodiment, when the siphoning apertures are much smaller than the size of blood cells, embodiments of the present disclosure can be used to separate blood plasma from whole blood.

As another example, while described in the context of a microstructure which is formed via injection molding, a person of ordinary skill in the art would understand that microfluidic devices formed by other microfabrication techniques would also benefit from the use of such a thin thermoplastic film to allow outgassing as described above. Such techniques include micromachining, microlithography, and hot embossing, as well as other microfabrication techniques known to a person of ordinary skill in the art.

Thus, such other embodiments and modifications are intended to fall within the scope of the present disclosure. Further, although the present disclosure has been described herein in the context of at least one particular implementation in at least one particular environment for at least one particular purpose, those of ordinary skill in the art will recognize that its usefulness is not limited thereto and that the present disclosure may be beneficially implemented in any number of environments for any number of purposes.

The invention claimed is:

1. A method for using a microfluidic device comprising:
   providing said microfluidic device comprising a microchannel, wherein said microchannel comprises at least one inlet and at least one outlet, and wherein said microfluidic device further comprises a plurality of microchambers connected to said microchannel by a plurality of siphon apertures, and a thermoplastic thin film disposed adjacent to a surface of said microfluidic device such that said thermoplastic thin film caps said microchannel, said plurality of microchambers, and said plurality of siphon apertures;
   filling said plurality of microchambers of said microfluidic device with a reagent by applying said reagent at a first pressure to said at least one inlet;
   applying a high pressure gas at a second pressure at said at least one inlet or at said at least one outlet to force gas within the plurality of microchambers to pass through said thermoplastic thin film capping said plurality of microchambers, said plurality of siphon apertures, and said microchannel, wherein said second pressure is greater than said first pressure; and
   applying a low pressure gas at a third pressure at said at least one inlet to introduce said low pressure gas into the microchannel without introducing said low pressure gas into said plurality of microchambers, wherein said third pressure is less than said second pressure.

2. The method of claim 1, wherein the method is performed using a single integrated machine.

3. The method of claim 1, further comprising providing a polymerase chain reaction (PCR) reagent comprising nucleic acid molecules to each of the plurality of microchambers.

4. The method of claim 3, further comprising performing PCR by thermal cycling said plurality of microchambers.

5. The method of claim 3, further comprising acquiring images of said plurality of microchambers.

6. The method of claim 4, further comprising counting a number of said plurality of microchambers within which said PCR successfully amplifies said nucleic acid molecules.

7. The method of claim 6, further comprising applying Poison statistics to said number of said plurality of microchambers within which said PCR successfully amplifies said PCR reagent to quantify nucleic acids within said PCR reagent.

8. The method of claim 1, wherein said microchannel comprises a plurality of sub-channels connected via a cross-channel and wherein said plurality of microchambers are connected to said plurality of sub-channels.

9. The method of claim 8, wherein the plurality of sub-channels are substantially parallel to one another such that said plurality of microchambers are in a grid configuration.

10. The method of claim 1, wherein said third pressure is between about 1 pound per square inch (psi) and 4 psi.

11. The method of claim 1, wherein said second pressure is between about 8 psi and 16 psi.

12. The method of claim 1, wherein said high pressure gas comprises air, nitrogen, carbon dioxide, a noble gas, or any combination thereof.

13. The method of claim 1, wherein said thermoplastic thin film comprises a cyclo-olefin polymer.

14. The method of claim 1, further comprising a pneumatic pump in fluid communication with said at least one inlet or said at least one outlet.

15. The method of claim 1, wherein said plurality of microchambers comprises between 1,000 and 20,000 microchambers.

16. The method of claim 1, wherein said plurality of microchambers are cylindrical in shape.

17. The method of claim 1, wherein said microfluidic device is formed by injection molding.

18. The method of claim 1, wherein said thermoplastic thin film is formed by injection molding.

* * * * *